United States Patent
Scott et al.

(10) Patent No.: US 6,673,926 B2
(45) Date of Patent: Jan. 6, 2004

(54) PROCESS OF PREPARING 3S-3-AMINO-3-ARYL PROPRIONIC ACID AND DERIVATIVES THEREOF

(75) Inventors: Lorraine Scott, North Wales, PA (US); Frank John Villani, Jr., Perkasie, PA (US); Donald G. Walker, Pipersville, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/021,369

(22) Filed: Oct. 29, 2001

(65) Prior Publication Data

US 2002/0068829 A1 Jun. 6, 2002

Related U.S. Application Data

(63) Continuation of application No. 09/531,637, filed on Mar. 21, 2000, now abandoned.
(60) Provisional application No. 60/126,227, filed on Mar. 22, 1999.

(51) Int. Cl.$^7$ .................... C07D 239/02; C07D 211/70; C07D 211/82
(52) U.S. Cl. .................. 544/335; 546/334; 546/335
(58) Field of Search ............... 546/334, 335; 544/335

(56) References Cited

U.S. PATENT DOCUMENTS

| | | | |
|---|---|---|---|
| 4,585,887 A | 4/1986 | Jolidon et al. | 560/38 |
| 5,254,573 A | 10/1993 | Bovy et al. | 514/357 |
| 5,840,961 A | 11/1998 | Behling et al. | 560/172 |

FOREIGN PATENT DOCUMENTS

| | | | | |
|---|---|---|---|---|
| DE | 10111877 | * | 9/2002 | |
| WO | WO 97/41102 | | 11/1997 | C07D/211/60 |
| WO | WO 98/02410 | | 1/1998 | C07C/227/32 |

OTHER PUBLICATIONS

CA 137:140741, abstract, Cohen, 2002.*
CA 137:304261, abstract, Dallemagne, 2002.*
J.G. Rico, R.J. Lindmark, T.E. Rogers, & P.R. Bovy, *A Highly Stereoselective Michael Addition to an a, β–Unsaturated Ester as the Crucial Step in the Synthesis of a Novel β–Amino Acid–Containing Fibrinogen Receptor Antagonist*, J. Org. Chem. 1993, 58, 7948–7951.

F.A. Davis, J.M. Szewczyk & R.E. Reddy, *An Efficient Synthesis of (S)–(+)–Ethyl β–Amino–3–pyridinepropanoate Using Enantiopure Sulfinimines*, J. Org. Chem. 1996, 61, 2222–2225.

T.P. Tang & J.A. Ellman, *The tert–Butanesulfinyl Group: An Ideal Chiral Directing Group and Boc–Surrogate for the Asymmetric Synthesis and Applications of β–Amino Acids*, J. Org. Chem. 1999, 64, 12–13.

E. Profft & F.J. Becker, *The Condensation of β–aryl–β–aminoacids with δ–valero– and ε–+ caprolactim Ethers and the Feasibility of Cyclization of the Condensation Products Obtained*, Journal für praktische Chemie, 4$^{th}$ series, vol. 30, 18–38 (1965). (with English translation).

Davies, Stephen G. & Ichihara, Osamu, Asymmetric Synthesis of R–β–Amino Butanoic Acid and S–β–Tyrosine: Homochiral Lithium Amide Equivalents for Michael Additions to α, β–Unsaturated Esters, Tetrahedron:Asymmetry, vol. 2, No. 3, pp. 183–186, 1991, Great Britain.

Zablocki, Jeffery A, et al., *Potent in Vitro and in Vivo Inhibitors of Platelet Aggregation Based Upon the Arg–Gly–Asp Sequence of Fibrinogen. (Aminobenzamidino)succinyl (ABAS) Series of Orally Active Fibrinogen Receptor Antagonists*, J. Med. Chem., 38, No. 13, pp. 2378–2394, 1995.

Hoekstra, William J. et al., Potent Orally Active GPIIb/IIIa Antagonists Containing a Nipecotic Acid Subunit. Structure–Activity Studies Leading to the Discovery of RWJ–533308, J. Med. Chem., 1999, 42, 5254–5265.

Zablocki, J.A., et al., *Potent in Vitro and in Vivo Inhibitors of Platelet Aggregation Based Upon the Arg–Gly–Asp Sequence of Fibrinogen. (Aminobenzamidino)succinyl (ABAS) Series of Orally Active Fibrinogen Receptor Antagonists*, J. Med. Chem., 1995, 38, 2378–2394.

* cited by examiner

*Primary Examiner*—D. Margaret Seaman

(57) ABSTRACT

The present invention is directed to a process for preparing 3S-3-amino-3-aryl propionic acid and derivatives thereof.

24 Claims, No Drawings

PROCESS OF PREPARING 3S-3-AMINO-3-ARYL PROPRIONIC ACID AND DERIVATIVES THEREOF

CROSS REFERENCE TO RELATED APPLICATIONS

This application is a continuation application of Ser. No. 09/531,637, filed Mar. 21, 2000 (now abandoned), which claims the benefit of U.S. Provisional Application No. 60/126,227, filed on Mar. 22, 1999.

FIELD OF THE INVENTION

The present invention is directed to a process for preparing 3S-3-amino-3-aryl propionic acid and derivatives thereof.

BACKGROUND OF THE INVENTION 3S-3-amino-3-aryl propionic acid derivatives of the formula I

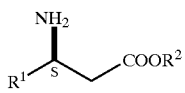

wherein
$R^1$ is aryl, heteroaryl, substituted aryl or substituted heteroaryl and $R^2$ is hydrogen, alkyl or aralkyl, or acid addition salts thereof, are useful as intermediates in the synthesis of compounds described in WO 97/41102, which is incorporated by reference herein. Compounds described in WO 97/41102 are antagonists of the platelet fibrinogen receptor (gp IIb/IIIa antagonist) and thus are useful for treating platelet-mediated thrombotic disorders such as arterial and venous thrombosis, acute myocardial infarction, reocclusion following thrombolytic therapy and angioplasty, inflammation, unstable angina and vaso-occlusive disorders.

Known methods for preparing compounds of Formula I include an asymmetric Michael addition of lithium N-(trimethylsilyl)-(R)-phenethylamide to ethyl 3-pyridyl acrylate to give the ethyl β-aminoester [Rico, J. G.; Lindmark, R. J.; Rogers, T. E.; Bovy, P. R. *J. Org. Chem.* 1993, 58, 7948]. This process results in inefficient formation of lithium amide and difficult removal of N-α-methylbenzyl group.

J. Org. Chem. vol. 61, p. 2222 (1996) discloses a process wherein the lithium enolate of ethyl acetate is added to an enantiomerically pure sulfinimine, the product of which is purified by chromatography and deprotected under acidic conditions to afford the β-amino ester in greater than 90% ee. The need for chromatography makes this process unattractive for large-scale production. Similarly, J. Org. Chem., vol 64, p. 12 (1999) discloses a process wherein a titanium enolate of methyl acetate is added to an enantiomerically pure t-butylsulfinimine to afford the β-amino ester in about 90% ee.

WO 98/02410 discloses a process of stereoselective addition of the Reformatsky reagent prepared from t-butylbromoacetate to the enantiomerically pure imine prepared from 3-pyridine carboxaldehyde and (R)-2-phenylglycinol. Oxidative cleavage of the N-(1-phenyl-2-hydroxy ethyl) group with $NaIO_4$ in ethanol followed by acid hydrolysis affords the enantiomerically pure t-butyl β-amino ester. Use of oxidizing agents makes this process unattractive for large-scale production.

WO 97/41102 discloses enzymatic resolution of the (±)β-phenylacetamido acid using penicillin amidase to afford the S-acid. This process, which utilizes enzymes, is inefficient and impractical for large scale production.

Thus there exists a need for a process which is compatible with large scale production needs and which achieves acceptable levels of purity and yield.

SUMMARY OF THE INVENTION

The invention is directed to a process of making a compound of formula I, as described above, comprising reacting a compound of formula II,

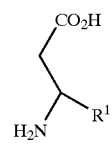

wherein $R^1$ is aryl, heteroaryl, substituted aryl or substituted heteroaryl, at a pH range of between about 7 and about 11, to form a compound of formula III

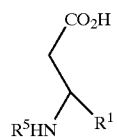

wherein $R^5$ is N-t-butoxycarbonyl,
reacting a compound of formula III with at least 0.5 equivalents of (1R,2S)-(−)-ephedrine, in an alkyl acetate solvent, to form a salt of formula IV

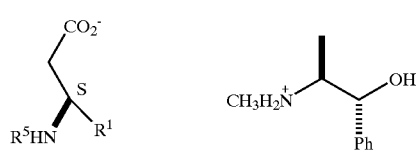

wherein Ph is phenyl, reacting the salt of formula IV with an inorganic base in water to form a carboxylate salt of the compound of formula V, acidifying the carboxylate salt of the compound of formula V with an acid of pKa less than or equal to three, to a pH of between about 3.5 and about 6.5, to form the compound of formula V

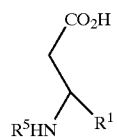

reacting the compound of formula V, at a temperature less than about 25° C., to form the compound of formula I.

In another aspect, the invention is directed to a novel crystal form of (3S)-3-[(tert-butoxy)carbonyl]amino-3-[3'-pyridyl]propionic acid, the intermediate of formula Va

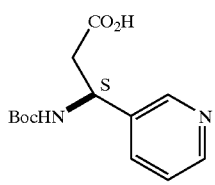

Va wherein Boc is (tert-butoxy)carbonyl designated Form 2 and characterized by its x-ray powder diffraction patterns.

DETAILED DESCRIPTION OF THE INVENTION

As used herein, unless otherwise noted, "alkyl" whether used alone or as part of a substituent group, shall include straight and branched chains containing 1 to 10 carbon atoms. For example, alkyl radicals include methyl, ethyl, n-propyl, isopropyl, n-butyl, isobutyl, sec-butyl, t-butyl, n-pentyl, n-hexyl and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted aromatic groups such as phenyl, napthyl, and the like. The aryl group may be substituted with one or two substituents. Suitable substituents on the aryl group are selected independently from the group consisting of halogen, alkyl, alkoxy, aralkyl, —$NR^3_2$, wherein $R^3$ is alkyl; and $R^4CONH$, wherein $R^4$ is phenyl or alkyl.

As used herein, unless otherwise noted, "heteroaryl" shall denote any five or six membered monocyclic ring structure containing at least one heteroatom selected from O, N and S or a bicyclic ring system wherein the heteroaryl is fused to an aryl group. Examples of suitable heteroaryl groups include, but are not limited to, pyrrolyl, pyridyl, pyrazinyl, pyrimidinyl, pyrazolyl, pyridazinyl, furanyl, pyranyl, imidazolyl, thiophenyl, oxazolyl, isothiazolyl, isoxazolyl, furazanyl, benzothienyl, benzofuranyl, indolyl, isoindolyl, indolizinyl, indazolyl, purinyl, isoquinolyl, quinolyl, isothiazolyl, and the like. The heteroaryl may be substituted with one or two substituents. Suitable substituents on the heteroaryl group are selected independently from the group consisting of halogen, alkyl, alkoxy, aralkyl, —$NR^3_2$, wherein $R^3$ is alkyl; and $R^4CONH$, wherein $R^4$ is phenyl or alkyl. The heteroaryl group may be attached at any heteroatom or carbon atom of the ring such that the result is a stable structure, except when the heteroaryl contains only one heteroatom, then the heteroaryl must be attached at a carbon atom.

Preferably, the heteroaryl is pyridyl. The preferred heteroaryl may be substituted with one or two substituents as described above. Most preferably, the pyridyl is unsubstituted.

As used herein, unless otherwise noted, "aralkyl" shall mean any alkyl group substituted with an aryl group such as phenyl, napthyl and the like.

As used herein, unless otherwise noted, "halogen" shall mean chlorine, bromine, fluorine and iodine.

As used herein, unless otherwise noted, "an acid of pKa less than or equal to three" includes monochloroacetic, dichloroacetic, trichloroacetic, hydrochloric, hydrobromic, hydroiodic, perchloric, picric, nitric, sulfuric, phosphoric, methanesulfonic, tosic, trifluoromethanesulfonic, trifluoracetic, potassium bisulfate, sodium bisulfate, citric and the like.

As used herein, unless otherwise noted, "inorganic base" shall mean a base having a monovalent cation component, such as lithium carbonate, sodium carbonate, potassium carbonate, lithium hydroxide, sodium hydroxide, potassium hydroxide, tetrabutyl ammonium hydroxide, trimethylbenzyl ammonium hydroxide and the like.

As used herein, unless otherwise noted, "alkyl alcohol" shall denote a hydroxy derivative of the above described straight or branched chain alkyl groups. For example, methanol, ethanol, N-propanol, isopropanol, isobutanol, t-butanol and the like.

As used herein, the notation "S" and "R" shall denote the presence of a stereogenic center having the S or R configuration.

In a preferred embodiment of the invention, in the compound of formula I, $R^1$ is unsubstituted phenyl, substituted phenyl, unsubstituted pyrimidyl, substituted pyrimidyl, unsubstituted pyridyl, substituted pyridyl, unsubstituted napthyl or substituted naphthyl. Suitable substituents are selected independently from the group consisting of halogen, alkyl, alkoxy, aralkyl, —$NR^3_2$, wherein $R^3$ is alkyl, and $R^4CONH$, wherein $R^4$ is phenyl or alkyl. More preferably, $R^1$ is 2-pyridyl, 3-pyridyl, 4-pyridyl, 6-methylpyridyl, 5-bromopyridyl, 6-chloropyridyl or 5,6-dichloropyridyl. Most preferably $R^1$ is 3-pyridyl. Preferably $R^2$ is alkyl, more preferably methyl or ethyl, most preferably methyl.

In an embodiment of the present invention, wherein the compound of formula I is present as an acid addition salt, the acid is an acid of pKa less than or equal to three, as defined above, other than potassium bisulfate, sodium bisulfate and citric acid. Preferably the compound of formula I is a hydrochloric acid addition salt.

The present invention is directed to a process of making a compound of formula I

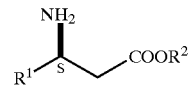

I wherein $R^1$ and $R^2$ are as described above, or acid addition salt thereof, which comprises reacting a compound of formula II

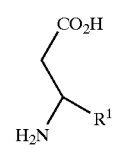

II to form a compound of formula III

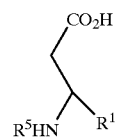

III wherein $R^5$ is N-t-butoxycarbonyl, reacting a compound of formula III to form a salt of formula IV

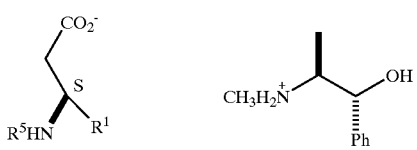

wherein Ph is phenyl, reacting the salt of formula IV to form the compound of formula V

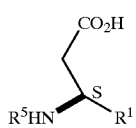

reacting the compound of formula V to form the compound of formula I.

In accordance with the invention, a compound of formula II, a known compound or compound prepared by known methods [Profft, V. E.; Becker, F. J., J. Prakt. *Chem.* 1965, 30(1–2), 18] is reacted with di-tert-butyl dicarbonate in an organic solvent such as 1,4-dioxane, tert-butanol or tetrahydrofuran, preferably tetrahydrofuran, with addition of an aqueous solution of an inorganic base, as previously defined, preferably sodium hydroxide, at a temperature in the range of about 0° to about 100° C., preferably at a temperature between about 0° and about 35° C., at a pH in the range of about 7 to about 11, preferably at a pH of between about 9.9 and about 10.2, to form the compound of formula III.

Preferably, the desired compound of formula III is isolated by removal of the organic solvent by evaporation under reduced pressure, followed by acidification of the remaining aqueous solution by addition of an acid of pKa of less than or equal to three, as defined above, preferably sodium bisulfate or citric acid, to a pH of between about 3.5 and about 6.5, preferably to a pH of about 3.8, filtration and extraction with an organic solvent, such as methylene chloride, 1,2-dichloroethane, chloroform, dioxane, toluene, alkyl acetate such as ethyl acetate or mixtures thereof, preferably ethyl acetate, and optionally removal of the organic solvent by evaporation under reduced pressure.

The compound of formula III is reacted with at least 0.5 equivalents of (1R,2S)-(−)ephedrine, preferably 0.5 to 1.0 equivalent of (1R,2S)-(−)ephedrine, in an alkyl acetate solvent, preferably ethyl acetate, at a temperature from about 25° to about 78° C., to form the salt of formula IV.

The salt of formula IV is reacted with an inorganic base, as previously defined, preferably, sodium hydroxide, in water to form a carboxylate salt of the compound of formula V (dissolved in the aqueous solution).

The desired compound of formula V is isolated by removal of the (1R,2S)-(−)ephedrine by extraction with an organic solvent which is largely immiscible with water such as methylene chloride, 1,2-dichloroethane, alkyl acetate or aromatic hydrocarbon, such as toluene, or ketone, such as methyl-isobutyl ketone, followed by acidification of the remaining aqueous solution by addition of an acid of pKa less than or equal to three, as defined above, preferably sodium bisulfate or sulfuric, to a pH of between about 3.5 and about 6.5, preferably to a pH of about 3.8, and filtration to afford the compound of formula V. When the organic solvent which is largely immiscible with water is toluene, preferably the aqueous solution containing the compound of formula V is heated to a temperature in the range of about 70–80° C. prior to extraction with the toluene and cooled to about room temperature after extraction with the toluene and prior to acidification.

The compound of formula V is reacted with an acid of pKa less than or equal to three, as defined above, other than potassium bisulfate, sodium bisulfate and citric acid, preferably hydrochloric acid, in a $C_1$–$C_{10}$ alkyl alcohol, preferably methanol, at a temperature less than about 25° C., to form the corresponding compound of formula I, which is isolated by conventional methods, such as filtration.

Form 2 of the compound of formula Va may be characterized by its x-ray powder diffraction pattern utilizing a Siemens D5000 diffractometer and the following system conditions:

a) CuKα radiation, 35 mA, 40 KV
b) Optics
 1 mm slit, Goebel mirrors, 0.6 mm slit, & vertical soller slits between tube and sample
 LiF monochromator between sample and detector
c) Scan 5 to 35°2θ at 0.02 Step Size at rate of 1°2θ/minute
d) Zero background sample holder

| Powder X-Ray Diffraction Results | | | |
|---|---|---|---|
| Angle 2θ | d value Angstrom | Intensity Cps | Intensity % |
| 5.186 | 17.028 | 1.67 | 0.1 |
| 5.405 | 16.338 | 4.17 | 0.2 |
| 6.069 | 14.550 | 163 | 6.2 |
| 6.526 | 13.532 | 1350 | 51.1 |
| 7.659 | 11.534 | 28.3 | 1.1 |
| 9.111 | 9.698 | 22.5 | 0.9 |
| 10.786 | 8.196 | 1417 | 53.6 |
| 13.073 | 6.767 | 83.3 | 3.2 |
| 15.660 | 5.654 | 659 | 25.0 |
| 17.063 | 5.192 | 1105 | 41.8 |
| 18.405 | 4.817 | 102 | 3.8 |
| 18.843 | 4.706 | 212 | 8.0 |
| 19.108 | 4.641 | 343 | 13.0 |
| 19.679 | 4.507 | 417 | 15.8 |
| 20.755 | 4.276 | 36.7 | 1.4 |
| 21.514 | 4.127 | 2641 | 100.0 |
| 22.796 | 3.898 | 652 | 24.7 |
| 23.944 | 3.713 | 101 | 3.8 |
| 24.363 | 3.650 | 340 | 12.9 |
| 25.502 | 3.490 | 89.2 | 3.4 |
| 25.640 | 3.471 | 89.2 | 3.4 |
| 26.265 | 3.390 | 172 | 6.5 |
| 26.786 | 3.326 | 98.3 | 3.7 |
| 27.770 | 3.210 | 1152 | 43.6 |
| 28.722 | 3.106 | 164 | 6.2 |
| 29.151 | 3.061 | 764 | 28.9 |
| 29.656 | 3.010 | 70.8 | 2.7 |
| 30.468 | 2.9315 | 58.3 | 2.2 |
| 31.214 | 2.8631 | 61.7 | 2.3 |
| 31.868 | 2.8058 | 61.7 | 2.3 |
| 32.301 | 2.7692 | 95.8 | 3.6 |
| 32.874 | 2.7222 | 147 | 5.6 |
| 33.480 | 2.6743 | 53.3 | 2.0 |
| 34.081 | 2.6285 | 122 | 4.6 |
| 34.626 | 2.5884 | 68.3 | 2.6 |

The following examples describe the invention in greater detail and are intended to illustrate the invention, but not to limit it.

EXAMPLE 1

3-Amino-3-(3'-Pyridyl)propionic acid

Part A

The reaction flask was charged with 300 g (264.3 mL)(2.8 mol) of cold 3-pyridine carboxaldehyde and 60 mL of absolute ethanol. A reaction temperature of 13° C. resulted. With good stirring, 291.36 g (2.8 mol) malonic acid was added in one portion (solid addition) over about 2 min, followed by 90 mL ethanol. Immediately following this addition, 323.73 g (4.2 mol) ammonium acetate was added over about 10 min (solid addition), followed by 250 mL ethanol. During this addition, the reaction cooled to about 38° C. The bright orange mixture was heated to and maintained under gentle reflux for 5 h. The heating mantle was removed, and the mixture was allowed to cool to ambient temperature overnight. The solid was collected by suction filtration (50 min) and washed with 400 mL methanol (30 min). The filtercake was washed with a second portion of 200 mL methanol (10 min). The filtercake was partially dried under suction for about 60 min. The solids were dried in vacuo at 35–40° C. to constant weight (38 h) to yield 303.38 g (65.2%) 3-amino-3-(3'-pyridyl)propionic acid as a white powder.

Part B

The reaction flask was charged with 594.52 g of a mixture of 3-amino-3-(3'-pyridyl)propionic acid and trans-3-(3'-pyridyl)acrylic acid and 1,600 mL methanol. With good stirring, the slurry was heated to and maintained under gentle reflux for 1.25 h. The slurry was filtered while hot, and was washed with 2×80 mL, then 160 mL warm (>50° C.) methanol (30 min). The filtercake was partially dried under suction for about 1.25 h. Further drying in vacuo at 35–40° C. for 21.5 h gave 540.22 g (90.9% weight recovery) product as a white powder.

The reaction flask was charged with 540.12 g of a mixture of 3-amino-3-(3'-pyridyl)propionic acid and trans-3-(3'-pyridyl)acrylic acid and 1,600 mL methanol. With good stirring, the slurry was heated to and maintained under gentle reflux for 5–6 h. The slurry was filtered while hot, and was washed with 3×160 mL warm (>50° C.) methanol (35 min). The filtercake was partially dried under suction for about 1.75 h yielding 814.45 g (>100% weight recovery) product as a white solid (wet cake).

The reaction flask was charged with 814.35 g of a mixture of 3-amino-3-(3'-pyridyl)propionic acid and trans-3-(3'-pyridyl)acrylic acid (wet cake) and 1,600 mL methanol. With good stirring, the slurry was heated to and maintained under gentle reflux for 3.75 h. The slurry was filtered while hot, and was washed with 3×160 mL warm (>50° C.) methanol (20 min). The filtercake was partially dried under suction for about 17.25 h. Further drying in vacuo at 40–45° C. for 20 h gave 390.69 g (65.7% weight recovery of original input) product as a white powder.

EXAMPLE 2

3-[(tert-Butoxy)carbonyl]amino-3-(3'-Pyridyl) propionic acid

The reaction flask was charged with 200 mL tetrahydrofuran and 170.88 g (1.03 mol) 3-amino-3-(3'-pyridyl)propionic acid and 614 mL tetrahydrofuran with good stirring. At ambient temperature (22° C.), 514 mL (1.03 mol) 2M sodium hydroxide solution was added in a slow pour over about 2 min. During this addition, the reaction temperature rose to 26° C. and most of the solid dissolved. After stirring an additional 45 min at ambient temperature, a slightly hazy, colorless solution resulted; pH 10.57 at 24° C. A 1 L constant pressure addition funnel was charged with 407 mL tetrahydrofuran (THF) and 365.3 mL (1.54 mol) di-tert-butyl dicarbonate. A second 1 L constant pressure addition funnel was charged with 771 mL (1.54 mol) 2M sodium hydroxide solution. The tetrahydrofuran solution of the di-tert-butyl dicarbonate was added in a slow stream over about 25 min with pH monitoring. Once the pH reached about 9.90, concomitant addition of the 2M sodium hydroxide solution was started. External cooling was applied to maintain the reaction temperature at <35° C. The reaction was maintained at pH 9.9–10.2 during the addition of the tetrahydrofuran/di-tert-butyl dicarbonate solution. Following its addition, the addition funnel which contained the dicarbonate/tetrahydrofuran solution was rinsed forward with 81 mL fresh tetrahydrofuran. Addition of the remaining amount of 2M sodium hydroxide solution was continued so as to maintain a pH in the range of 9.9–10.2. Following addition of the remaining amount of 2M sodium hydroxide solution, the pH probe was removed and the reaction was stirred at ambient temperature for 17 h. With good stirring, the pH was lowered from 7.68 at 21° C. to 3.87 at 27° C. by portionwise addition of 393.0 g (2.85 mol) of sodium bisulfate monohydrate over about 3 h. The heterogeneous mixture was cooled 75 min in an ice water bath with good stirring. A volume of 1,285 mL water was marked on the outside of a 5 L wide-mouth round-bottom flask while mounted on the rotary evaporator. The flask was emptied, then refilled with the reaction slurry. The reaction flask was rinsed forward with 2×250 mL 98/2(v/v) tetrahydrofuran-water solution. The slurry was concentrated at 25° C. for about 3 h to a volume of about 1,285 mL. The concentrated mixture was extracted with 4×650 mL of methylene chloride. The combined extracts were dried 45 min over 23.5 g (0.20 mol) anhydrous magnesium sulfate with good stirring. After filtration, the clear, colorless filtrate was concentrated over 90 min at 25° C. to a mobile syrup. This was carefully concentrated further for 45 min at 35° C. and at <5 mm Hg to a thick syrup. Further drying in vacuo at ambient temperature for 60 h gave 227.24 g (83.0%) product as a clear, immobile glass. By $^1$H NMR spectroscopy, this material was assigned a purity of 89.8 w/w%.

EXAMPLE 3

(3S)-3-[(tert-Butoxy)carbonyl]amino-3-(3'-pyridyl) propionic acid, (1R,2S)-(−)-ephedrine salt Part A The reaction flask was charged with 2,750 mL ethyl acetate and 227.23 g (0.77 mol) 3-[(tert-butoxy)carbonyl] amino-3-(3'-pyridyl)propionic acid. With good stirring, the solution was heated to a reaction temperature of 62° C. A freshly prepared solution of 126.9 g (0.77 mol) (1R,2S)-(−)-ephedrine in 350 mL ethyl acetate was added in a slow stream over about 9 min at 64° C. The addition funnel which contained the ephedrine solution was rinsed forward with 50 mL ethyl acetate. The clear, colorless solution (63° C.) was seeded. Within 1–2 min, heavy precipitation of the product commenced. (During crystallization the agitation speed was increased to maintain good stirring of the slurry). The slurry was slowly cooled to ambient temperature. After about 18 h, the solid was collected by suction filtration and washed with 2×125 mL fresh ethyl acetate (15 min). The filtercake was partially dried under suction for 35 min. Further drying in vacuo at 40–45° C. for 21 h gave 153.04 g (46.3%) product as a fluffy white solid.

Part B

The reaction flask was charged with 415.33 g (0.96 mol) (3S)-3-[(tert-butoxy)carbonyl]amino-3-(3'-pyridyl) propionic acid, (1R,2S)-(−)-ephedrine salt and 9 L ethyl acetate. The resulting slurry was heated and maintained under gentle reflux for 30 min with good stirring. The slurry was allowed to cool slowly to ambient temperature with continued good stirring. After 15 h, 250 mL fresh ethyl acetate was added to restore good agitation. After an additional 2 h, the solid was collected by suction filtration and washed with 2×450 mL fresh ethyl acetate (10 min). The filtercake was partially dried under suction for 75 min. Further drying in vacuo at 50–55° C. for 44 h gave 311.25 g (74.9%) product as a fluffy white solid.

EXAMPLE 4

(3S)-3-[(tert-Butoxy)carbonyl]amino-3-(3'-Pyridyl) propionic acid

The reaction beaker was charged with 303.47 g (0.67 mol) (3S)-3-[(tert-butoxy)carbonyl]amino-3-(3'-pyridyl) propionic acid, (1R,2S)-(−)-ephedrine salt and 792 mL milliquat water. After stirring 5 min, the pH of the slurry was 7.32 at 21° C. A total of 595 mL (0.60 mol) 1M sodium hydroxide solution was added in a slow pour over about 2 min with good stirring to a pH of 11.00 at 23° C. After an additional 5 min (pH 10.86), 20 mL (0.02 mol) 1M sodium hydroxide solution was added with continued good stirring to a pH of 11.00 at 23° C. After stirring an additional 65 min (pH 10.73 at 22° C.), 50 mL (0.05 mol) 1M sodium hydroxide solution was added to pH 11.07 at 22° C. The slightly hazy, colorless solution was washed with 12×880 mL methylene chloride. Following the last wash, the pH was 7.76 at 20° C. With good stirring, 47.89 g (0.35 mol) sodium bisulfate monohydrate was added portionwise over 10 min to pH 5.18 at 21° C. The cloudy solution was seeded and the developing slurry was stirred for 5 min. During this crystallization, the pH increased to 5.76 at 21° C. Next was added 47.82 g (0.34 mol) sodium bisulfate monohydrate over 25 min to pH 3.79 at 22° C. The slurry was cooled 40 min in an ice water bath, filtered (5 min) and partially dried under suction for 20 min. The filtercake was dried in vacuo at 50–55° C. for 17 h to yield 151.72 g (85.1%) product as a colorless, crystalline solid.

EXAMPLE 5

Methyl (3S)-3-Amino-3-(3'-pyridyl) propionate dihydrochloride

A round-bottom flask was charged with 142.01 g (0.53 mol) (3S)-3-[(tert-butoxy)carbonyl]amino-3-(3'-pyridyl) propionic acid and 1,350 mL methanol. The mixture was spun, without vacuum, on a rotary evaporator at 25° C. for 2 h, then carefully concentrated to a colorless mobile syrup. This syrup was transferred into the reaction flask using 1,350 mL methanol. The opaque solution was cooled in an ice water bath to 0–5° C. Next, about 194.4 g (5.33 mol) hydrogen chloride was bubbled into the solution over about 3 h. During this addition, the reaction temperature was kept at <15° C. Following seeding, the slurry was warmed to ambient temperature and stirred for 2 h. The slurry was cooled 30 min in an ice water bath. The solid was collected by suction filtration and washed with 2×65 mL cold (0–5° C.) methanol (5 min). The filtercake was partially dried under suction for about 20 min. Further drying in vacuo at ambient temperature for 14 h gave 105.21 g (77.9%) product as a white, crystalline powder.

EXAMPLE 6

3-Amino-3-[3'-(6-methyl)pyridyl]propionic acid

To a mixture of 6-methylpyridine-3-carboxaldehyde (23.5 g, 0.149 mol), ammonium acetate (22.9 g, 1.5 eq.) and ethanol (350 mL) was added malonic acid (20.5 g, 1 eq.). The mixture was heated under reflux for 6 h, cooled to room temperature and filtered. This filtered solid was washed with ethanol (2×30 mL) and diethyl ether (2×100 mL) and dried to give the product as a white solid (23.2 g, 66% yield).

EXAMPLE 7

3-Amino-3-[3'-(5-bromo)pyridyl]propionic acid

To a mixture of 5-bromopyridine-3-carboxaldehyde (40.4 g, 0.21 mol), ammonium acetate (24.3 g, 1.5 eq.) and absolute ethanol (650 mL) was added malonic acid (21.8 g, 1 eq.). The mixture was heated under reflux for 6.5 h, cooled to room temperature and filtered. This filtered solid was washed with ethanol and diethyl ether and dried to a crude product (28.0 g, 55% yield). This solid was heated under reflux for 30 min in methanol (500 mL), filtered hot, washed with hot methanol and dried to give the product as a white solid (17.4 g; 34%).

EXAMPLE 8

3-Amino-3-[3'-(6-chloro)pyridyl]propionic acid

To a mixture of 6-chloropyridine-3-carboxaldehyde (32.6 g, 0.229 mol), ammonium acetate (26.5 g, 1.5 eq.) and absolute ethanol (300 mL) was added malonic acid (23.8 g, 1 eq.). The mixture was heated under reflux for 2.5 h, cooled to room temperature and filtered. This filtered solid was washed with ethanol and diethyl ether and dried to a crude product (30.6 g, 66% yield). This solid was heated under reflux in methanol (500 mL), filtered hot, washed with hot methanol (3×150 mL) and diethyl ether and dried to give the title compound (24.5 g; 53%). This solid was heated under reflux in methanol (500 mL), filtered hot, washed with hot methanol and diethyl ether and dried to give the product as a white solid (21.0 g; 46%).

EXAMPLE 9

3-Amino-3-[3'-(5,6-dichloro)pyridyl]propionic acid

To a mixture of 5, 6-dichloropyridine-3-carboxaldehyde (9.4 g, 0.053 mol), ammonium acetate (6.2 g, 1.5 eq.) and absolute ethanol (100 mL) was added malonic acid (5.6 g, 1 eq.). The mixture was heated under reflux for 8 h, cooled to room temperature, stirred overnight and filtered. This filtered solid was washed with ethanol and diethyl ether and dried to a crude product (7.0 g, 56% yield). This solid was heated under reflux in methanol (125 mL) for 15 min, filtered hot, washed with hot methanol (50 mL) and dried to give the product as a white solid (4.4 g; 35%).

EXAMPLE 10

3-[(tert-butoxy)carbonyl]amino-3-[3'-(6-methyl) pyridyl]propionic acid

To a cooled (5° C.) solution of 3-amino-3-[3'-(6-methyl) pyridyl]propionic acid (23.2 g, 0.128 mol), 1 N sodium hydroxide (256 mL, 2 eq.), and dioxane (150 mL) was added di-tert-butyl dicarbonate (27.9 g, 1 eq.). This mixture was stirred for 1.5 h, the ice bath removed, and stirring continued for 16 h. The dioxane was removed in vacuo, and the resultant aqueous mixture adjusted to pH 4 with 10% citric acid (250 mL). This solution was cooled in an ice bath, stirred for 30 min, and filtered to give 7.7 g white powder. The filtrate was reduced to half volume in vacuo, treated with sodium chloride (30 g), cooled for 70 h, and filtered to give a second crop (22.4 g) of product. The crops were combined to give the product as a white solid (30.1 g, 84% yield).

EXAMPLE 11

3-[(tert-butoxy)carbonyl]amino-3-[3'-(5-bromo) pyridyl]propionic acid

To a cooled (5° C.) solution of 3-amino-3-[3'-(5-bromo) pyridyl]propionic acid (17.4 g, 0.071 mol), 1 N sodium hydroxide (142 mL, 2 eq.), and dioxane (100 mL) was added di-tert-butyl dicarbonate (15.5 g, 1 eq.). This mixture was allowed to warm to ambient temperature and was stirred overnight. The dioxane was removed in vacuo, and the resultant aqueous mixture adjusted to pH 3–4 with 10% citric acid. This solution was extracted with 9/1 (v/v) chloroform—dioxane (3×150 mL), and the combined extracts were dried over anhydrous sodium sulfate, filtered and concentrated to give the product as a white solid (21.1 g, 86%).

EXAMPLE 12

3-[(tert-butoxy)carbonyl]amino-3-[3'-(6-chloro) pyridyl]propionic acid

To a cooled (5° C.) solution of 3-amino-3-[3'-(6-chloro) pyridyl]propionic acid (21.0 g, 0.105 mol), 1 N sodium hydroxide (210 mL, 2 eq.), and dioxane (150 mL) was added di-tert-butyl dicarbonate (22.89 g, 1 eq.). This mixture was allowed to warm to ambient temperature and was stirred overnight. The dioxane was removed in vacuo, and the resultant aqueous mixture adjusted to pH 3–4 with 10% citric acid. The mixture was filtered and the solids were washed with water and air dried overnight to give the product as a white solid (21.5 g, 68%).

EXAMPLE 13

3-[(tert-butoxy)carbonyl]amino-3-[3'-(5,6-dichloro) pyridyl]propionic acid

To a cooled (5° C.) solution of 3-amino-3-[3'-(5,6-dichloro)pyridyl]propionic acid (4.4 g, 0.019 mol), 1 N sodium hydroxide (37.6 mL, 2 eq.), and dioxane (30 mL) was added di-tert-butyl dicarbonate (4.1 g, 1 eq.). This mixture was allowed to warm to ambient temperature and was stirred overnight. The dioxane was removed in vacuo, and the resultant aqueous mixture adjusted to pH 3–4 with 10% citric acid. After additional stirring at ambient temperature, the mixture was filtered, solids were washed with water and air dried to give the product as a white solid (5.0 g, 79%).

EXAMPLE 14

(3S)-3-[(tert-butoxy)carbonyl]amino-3-[3'-(6-methyl)pyridyl]propionic acid, (1R,2S)-(−)-ephedrine salt To a slurry of 3-[(tert-butoxy)carbonyl]amino-3-[3'-(6-methyl)pyridyl]propionic acid (3.85 g, 0.0137 mol) and warm ethyl acetate (170 mL) was added a solution of (1R,2S)-(−)-ephedrine (2.31 g, 1 eq.) in ethyl acetate (60 mL). This mixture was heated to reflux to give a clear solution. After 5 min at ambient conditions, the warm solution was seeded and allowed to cool to room temperature. Crystallization of the salt began when the solution had reached 30° C. After crystallization for 15 min, the mixture was filtered, and the solid product washed with ethyl acetate (50 mL) and diethyl ether (50 mL) and dried to afford a white powder (1.9 g, 31% yield).

A second crop was isolated from the mother liquors after 16 h at ambient conditions (0.33 g, 5.4% yield). The two crops were combined, slurried with warm ethyl acetate (60 mL), and filtered to give 2.2 g (36%) of the product as a white solid.

EXAMPLE 15

(3S)-3-[(tert-butoxy)carbonyl]amino-3-[3'-(5-bromo) pyridyl]propionic acid, (1R,2S)-(−)-ephedrine salt To a solution of 3-[(tert-butoxy)carbonyl]amino-3-[3'-(5-bromo)pyridyl]propionic acid (21.0 g, 0.061 mol) and ethyl acetate (125 mL) was added (1R,2S)-(−)-ephedrine (10.1 g, 1 eq.), giving a clear solution. After seeding and standing overnight at ambient temperature, the mixture was filtered, the solid product washed with cold ethyl acetate and diethyl ether and dried to afford the product as a white powder (8.3 g, 27% yield).

EXAMPLE 16

(3S)-3-[(tert-butoxy)carbonyl]amino-3-[3'-(6-chloro) pyridyl]propionic acid, (1R, 2S)-(−)-ephedrine salt To a slurry of 3-[(tert-butoxy)carbonyl]amino-3-[3'-(6-chloro)pyridyl]propionic acid (21.4 g, 0.071 mol) and ethyl acetate (250 mL) was added (1R,2S)-(−)-ephedrine (11.79 g, 1 eq.). This mixture was heated to reflux to give a clear solution. The solution was cooled to room temperature and seeded. Following crystallization, additional ethyl acetate (700 mL) was added, the slurry was heated to boiling and then slowly cooled to ambient temperature. After stirring overnight, the mixture was filtered, the solid product washed with ethyl acetate and diethyl ether and dried to afford the product as a fluffy white solid (15.36 g, 46% yield).

EXAMPLE 17

(3S)-3-[(tert-butoxy)carbonyl]amino-3-[3'-(5,6-dichloro)pyridyl]propionic acid, (1R,2S)-(−)-ephedrine salt To a slurry of 3-[(tert-butoxy)carbonyl]amino-3-[3'-(5,6-dichloro)pyridyl]propionic acid (4.9 g, 0.015 mol) and ethyl acetate (150 mL) was added (1R,2S)-(−)-ephedrine (2.42 g, 1 eq.). This mixture was heated to reflux and filtered to remove a small amount of insoluble material. The clear filtrate was slowly cooled to ambient temperature. The mixture was filtered, the solid product washed with ethyl acetate and diethyl ether and dried to give a crude product (3.1 g). Recrystallization from boiling ethyl acetate (75 mL) returned the product as a white solid (2.8 g, 38%).

EXAMPLE 18

3-Amino-3-(3'-pyridyl)propionic acid

Ammonium acetate (194.28 g, 2.52 mol) was suspended in ethanol (285 g). A solution of pyridine-3-carbaldehyde (62.9 g, 1.68 mol) in ethanol (80 g) was added to the suspension within 10 min at 15° C.–20° C. The reaction mixture was stirred for 1 h until a clear yellowish solution was formed. A suspension of malonic acid (174.86 g, 1.68 mol) in ethanol (235 g) was then added (within 30 min.) After stirring for 30 min at ambient temperature the reaction mixture was heated for 5 h to reflux (78° C.). Gas evolution was observed. After 3–4 h a white solid started to precipitate. The orange colored suspension was cooled to 15° C.–20° C., and a thick slurry was obtained. To this slurry was added methanol (80 g) and the reaction mixture was again heated to reflux (65° C.). The suspension was filtered hot, and the filtercake was washed with three portions of hot methanol (120 g) (at a temperature of 55° C.–65° C.). The wet product was dried in vacuo at 70° C.–80° C. to yield the product as a colorless solid (137.73 g, 49.3%). LC purity 95.8%

EXAMPLE 19

3-[(tert-Butoxy)carbonyl]amino-3-(3-pyridyl) propionic acid

3-Amino-3-(3'-pyridyl)propionic acid (73.00 g, 0.439 mol) was suspended in THF (239.5 g) at 15° C.–25° C. Within 10–20 min a solution of sodium hydroxide (43.93 g, 1.10 mol) in purified water (395.4 g) was added, resulting in a slightly yellowish solution. Within 2–3 h a solution of BOC-anhydride (143.82 g, 0.659 mol) in THF (124.2 g) was added, while maintaining the solution temperature at no more than 30° C. The solution was stirred overnight (about 17 h) at 15° C.–25° C. Within 1–2 h a solution of sodium hydrogensulphate monohydrate (167.9 g, 1.22 mol) in water (160 g) was added to adjust the pH to about 3.8–3.9. Some solids were observed to precipitate, with strong evolution of gas. The suspension was cooled to 5° C.–10° C., filtered and washed with THF (50 g). The unified filtrates were reduced by distillation to one third of their original volume. Ethylacetate (102.9 g) was then added, an equal volume was distilled off, ethylacetate (99.4 g) was again added, and the same volume was distilled off. To the resulting aqueous emulsion were added sodium chloride (64.6 g) and ethylacetate (100.5 g). The phases were separated, and the aqueous phase was washed with ethylacetate (3×20 g). The unified organic phases were dried over sodium sulphate anhydrous (20 g), the drying agent was filtered off, and the filter cake washed with ethylacetate (5 g). The resulting solution (about 250 g) was used directly for the following step.

EXAMPLE 20

(3S)-3-[(tert-Butoxy)carbonyl]amino-3-(3'-pyridyl) propionic acid, (1R,2S)-(−)-ephedrine salt A solution of 3-[(tert-butoxy)carbonyl]amino-3-(3'-pyridyl)propionic acid (250 g) in ethylacetate containing 3-[(tert-Butoxy)carbonyl]amino-3-(3'-pyridyl)propionic acid (71.5 g, 0.269 mmol) and ethylacetate (178.5 g) was heated to 60° C.–70° C. Within 10 min a solution of (−)-ephedrine (48.80 g, 0.295 mol) in ethylacetate (90.0 g) was added. The clear solution was cooled to 20° C.–30° C. while the product crystalllized as a voluminuous, white solid. After the crystallization had started, ethylactate (270 g) was added to keep the mixture stirrable. The suspension was cooled to 15° C.–25° C., stirred for 3–5 h, and the solids collected by filtration. The filter cake was washed with ethylacetate (90 g) in two portions and dried in vacuo at 70° C.–80° C. to yield the product as a colorless solid (52.72 g, 28%). LC purity >99%

EXAMPLE 21

(3S)-3-[(tert-Butoxy)carbonyl]amino-3-(3'-pyridyl) propionic acid (3S)-3-[(tert-Butoxy)carbonyl]amino-3-(3'-pyridyl) propionic acid (1R,2S)-(−)-ephedrine salt (25.11 g, 0.058 mol) was dissolved in water (50.0 g) at 15° C.–25° C. Within 10–20 min a solution of sodium hydroxide (2.63 g, 0.066 mol) in water (23.3 g) was added, resulting in a clear solution. Toluene (17.4 g) was added under good stirring and the resulting emulsion was heated to 70° C.–80° C. After the stirring was stopped, the clear organic phase was separated from the slightly turbid aqueous phase. The aqueous phase was extracted with toluene (4×17.4 g) at 70° C.–80° C. The aqueous phase was then cooled to 15° C.–25° C., filtered, and the filter washed with water (2.5 g). To the unified filtrates was added a solution of sodium hydrogensulphate monohydrate (9.50 g, 0.069 mol) in water (12.1 g), resulting in a pH of 3.6–3.9 and crystallized product. The reaction mixture was cooled to 0° C.–5° C., stirred for 1 h further, and the product collected by filtration, washed with water (5 g) in two portions, dried in vacuo at 40° C.–50° C. to yield the product as a colorless solid (11.08 g, 72%). LC purity >95%

EXAMPLE 22

Methyl (3S)-3-amino-3-(3'-pyridyl)propioniate dihydrochloride (3S)-3-[(tert-butoxy)carbonyl]amino-3-(3'-pyridyl)propionic acid (9.93 g, 0.037 mol) was dissolved in methanol (45.8 g) at 0° C.–5° C. Within 2–3 h hydrogen chloride (34.2 g, 0.938 mol) was bubbled through the solution, while maintaining the temperature of the solution below about 15° C. After the addition of hydrogen chloride was complete, the reaction mixture was stirred for at least 2 h at 20° C.–25° C. and then cooled to 0° C.–5° C. After stirring for 30 min at 0° C.–5° C. the solids were collected by filtration, washed with cold methanol (14.2 g) (at a temperature of about 0° C.–5° C.) in two portions, and dried in vacuo at 20° C.14 30° C. to yield the product as a colorless solid (7.86 g, 83%). LC purity >95%

What is claimed is:

1. A process of preparing the compound of formula

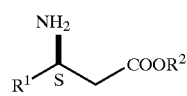

I wherein

R¹ is pyrimidyl optionally substituted with one or two substituents selected independently from the group consisting of halogen, alkyl, alkoxy, aralkyl, —NR³₂, wherein R³ is alkyl and R⁴ CONH wherein R⁴ is phenyl or alkyl, or pyridyl optionally substituted with one or two substituents selected independently from the group consisting of halogen, alkyl, alkoxy, aralkyl, —NR³₂, wherein R³ is alkyl and R⁴ CONH wherein R⁴ is phenyl or alkyl and R² is hydrogen, alkyl or aralkyl, or acid addition salts thereof, comprising reacting a compound of formula II, at a pH range of between about 7 and about 11,

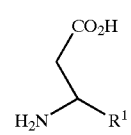

II to form a compound of formula III

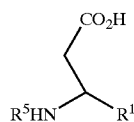                                         III wherein R⁵ is N-t-butoxycarbonyl,
reacting a compound of formula III with at least 0.5 equivalents of (1R,2S)-(−)ephedrine, in an alkyl acetate solvent, to form a salt of formula IV

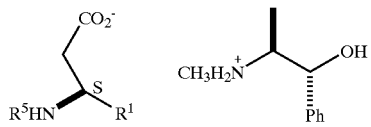                                         IV wherein Ph is phenyl,
reacting the salt of formula IV with an inorganic base in water to form a carboxylate salt of the compound of formula V, acidifying the carboxylate salt of the compound of formula V with an acid of pKa less than or equal to three, to a pH of between about 3.5 and about 6.5, to form the compound of formula V

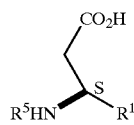                                         V reacting the compound of formula V, at a temperature less than about 25° C., to form the compound of formula I.

2. A process of preparing a compound of formula I

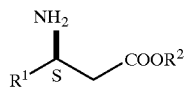                                         I wherein
R¹ is pyrimidyl optionally substituted with one or two substituents selected independently from the group consisting of halogen, alkyl, alkoxy, aralkyl, —NR³₂, wherein R³ is alkyl and R⁴CONH wherein R⁴ is phenyl or alkyl, or pyridyl optionally substituted with one or two substituents selected independently from the group consisting of halogen, alkyl, alkoxy, aralkyl, —NR³₂, wherein R³ is alkyl and R⁴CONH wherein R⁴ is phenyl or alkyl and R² is hydrogen, alkyl or aralkyl, or acid addition salts thereof,
comprising reacting a compound of formula III

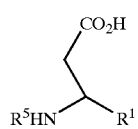                                         III with at least 0.5 equivalents of (1R,2S)-(−)ephedrine, in alkyl acetate solvent, to form a salt of formula IV

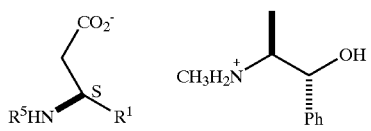                                         IV wherein Ph is phenyl,
reacting the salt of formula IV with an inorganic base, in water, to form a carboxylate salt of the compound of formula V, acidifying the carboxylate salt of the compound of formula V with an acid of pKa less than or equal to three, to a pH of between about 3.5 and about 6.5, to form the compound of formula V

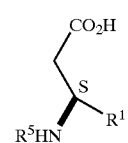                                         V reacting the compound of formula V, at a temperature less than about 25° C. to form the compound of formula I.

3. A process of claim 1, further comprising isolating the compound of formula III by acidifying the compound of formula III with an acid of pKa less than or equal to three, to a pH of between about 3.5 and about 6.5.

4. A process of claim 1, wherein the alkyl acetate solvent is ethyl acetate.

5. A process of claim 1, wherein the reaction of formula III with (1R,2S)-(−)ephedrine occurs at a temperature in the range of from about 25° to about 78° C.

6. A process of claim 1, further comprising acidifying the carboxylate salt of the compound of formula V with an acid of pKa less than or equal to three, to a pH of about 3.8, to form the compound of formula V.

7. A process of claim 1, wherein the acid of pKa less than or equal to three is selected from the group consisting of monochloroacetic, dichloroacetic, trichloroacetic, hydrochloric, hydrobromic, hydroiodic, perchloric, picric, nitric, sulfuric, phosphoric, methanesulfonic, tosic, trifluoromethanesulfOrlic, trifluoracetic, potassium bisulfate, sodium bisulfate and citric.

8. A process of claim 1, further comprising reacting the compound of formula V with an acid of pKa less than or equal to three, other than potassium bisulfate, sodium bisulfate and citric acid.

9. A process of claim 2, further comprising acidifying the compound of formula III with an acid of pKa less than or equal to three, to a pH of between about 3.5 and about 6.5.

10. A process of claim 2, wherein the alkyl acetate solvent is ethyl acetate.

11. A process of claim 2, wherein the reaction of formula III with (1R,2S)-(−)ephedrifle occurs at a temperature from about 25° to about 78° C.

12. A process of claim 2, further comprising acidifying the carboxylate salt of the compound of formula V with an acid of pKa less than or equal to three, to a pH of about 3.8, to form the compound of formula V.

13. A process of claim 2, wherein the acid of pKa less than or equal to three is selected from the group consisting of monochloroacetic, dichloroacetic, trichloroacetic, hydrochloric, hydrobromic, hydroiodic, perchloric, picric, nitric, sulfuric, phosphoric, methanesulfonic, tosic, trifluoromethanesulfonic, trifluoracetic, potassium bisulfate, sodium bisulfate and citric.

14. A process of claim 2, further comprising reacting the compound of formula V with an acid of pKa less than or equal to three, other than potassium bisulfate, sodium bisulfate and citric acid.

15. A process of claim 1, wherein $R^1$ is 2-pyridyl, 3-pyridyl, 4-pyridyl, 6-methylpyridyl, 5-bromopyridyl, 6-chloropyridyl or 5,6-dichloropyridyl.

16. A process of claim 2, wherein $R^1$ is 2-pyridyl, 3-pyridyl, 4-pyridyl, 6-methylpyridyl, 5-bromopyridyl, 6-chloropyridyl or 5,6-dichloropyridyl.

17. A process of claim 1, wherein $R^2$ is alkyl.

18. A process of claim 2, wherein $R^2$ is alkyl.

19. A process of claim 1, wherein $R^1$ is 3-pyridyl.

20. A process of claim 2, wherein $R^1$ is 3-pyridyl.

21. A process of claim 1, wherein $R^1$ is 3-pyridyl and $R^2$ is methyl.

22. A process of claim 2, wherein $R^1$ is 3-pyridyl and $R^2$ is methyl.

23. A process of claim 1, wherein the acid addition salt of formula I is hydrochloric.

24. A process of claim 2, wherein the acid addition salt of formula I is hydrochloric.

* * * * *